United States Patent [19]

Oppico et al.

[11] Patent Number: 4,861,870
[45] Date of Patent: Aug. 29, 1989

[54] PROCESS FOR PURIFYING ANTHRACYCLINONE GLYCOSIDES BY SELECTIVE ADSORPTION ON RESINS

[75] Inventors: Ernesto Oppico, Milan; Carlo Varesio; Onorino G. Rosa, both of Turin, all of Italy

[73] Assignee: Farmitalia Carlo Erba S.p.A., Italy

[21] Appl. No.: 9,550

[22] Filed: Feb. 2, 1987

Related U.S. Application Data

[63] Continuation of Ser. No. 758,838, Jul. 25, 1985, abandoned, which is a continuation of Ser. No. 563,136, Dec. 19, 1983, abandoned.

[30] Foreign Application Priority Data

Dec. 23, 1982 [IT]  Italy ............................... 24939 A/82

[51] Int. Cl.⁴ ...................... C07M 1/06; C07M 15/24
[52] U.S. Cl. .................................. 536/16.9; 536/6.4; 536/127

[58] Field of Search .................. 536/69, 16.9, 12.7

[56] References Cited

U.S. PATENT DOCUMENTS 2,793,978  5/1957  Wachtel et al. ............... 536/16.9
2,827,417  3/1958  Friedman et al. ............. 536/16.9
2,960,437  11/1960  Friedman et al. ............. 536/16.9
3,221,008  11/1965  Wolf et al. .................... 536/16.9
4,091,201  5/1978  Argoudelis et al. ........... 536/16.9

Primary Examiner—Johnnie R. Brown
Assistant Examiner—Elli Peselev
Attorney, Agent, or Firm—Sheldon Palmer

[57] ABSTRACT

Disclosed is a process for purifying an impure anthracyclinone glycoside by selective adsorption of a slightly acidic aqueous solution of an impure glycoside on at least one resin and subsequent de-absorption of the purified glycoside by elution with acidic water or a mixture of water and a polar solvent.

6 Claims, No Drawings

PROCESS FOR PURIFYING ANTHRACYCLINONE GLYCOSIDES BY SELECTIVE ADSORPTION ON RESINS

This application is a continuation of application Ser. No. 758,838, filed 7/25/85, now abandoned, which is a continuation of application Ser. No. 563,136 filed 12/19/83, now abandoned.

BACKGROUND OF THE INVENTION

1. Field of the Invention

The present invention relates to processes for purifying anthracyclinone glycosides by selective adsorption on resins.

2. The Prior Art

It is extremely desirable to have a highly specific method for obtaining anthracyclinone glycosides in a substantially pure form. This is so because in both the fermentative production processes and synthetic preparation processes the amount of organic and inorganic impurities present in the crude product is particularly high and averages from 12% to 25%.

The conventional methods of purifying these glycosides that have been hitherto used in known purification techniques involve the extraction of the crude produce with chlorinated solvents and subsequent washing with buffers. These techniques however lead to a final product in which the impurity percentage, although considerably lowered, is in the range of between 4.5 and 5.0%.

While such a level of impurity might be generally deemed acceptable, under certain circumstances it is not acceptable when considering the particular sensitivity of the anthracyclinone glycoside molecule to physical handling and chemical agents. All of this stimulated our interest in the search for an improved purification method which would enable us to obtain a substantially pure final product. Bearing in mind the particular clinical use of the anthracyclinone glycosides as antitumor agents, and the related problems of dosage and toxicity, the need for maximum elimination of impurities (which are generally highly toxic) is evident.

SUMMARY OF THE INVENTION

The invention provides a process for purifying impure preparations of anthracyclinone glycosides whereby one obtains a final product containing impurities in a maximum amount of 2%. According to the process, an impure preparation of an anthracyclinone glycoside is adsorbed on one or more types of resins in an acidic environment (pH=3-5) and subsequently eluted with water or a mixture of water and a polar solvent. More particularly, the process of the present invention involves a stage in which a slightly acidic phase containing the water soluble dissolved glycoside is adsorbed on the resin in the form of particles, such as granules or beads and a succeeding stage of de-adsorption of the glycoside that had been adsorbed in the first stage.

The adsorbing resin may be contained in a suitable container or vessel which is generally in the shape of a tower or column conveniently filled with resin particles. Depending on the type of impurities contained in the impure product, the eluate obtained by de-adsorption of the material from a first type of resin can be conveniently successively adsorbed on different type resin and then eluted therefrom by a known method.

In the chromatographic purification method of the invention, use is made of adsorbing resins of the polymeric and ion exchange types or a carboxymethylcellulose type resin. The correct selection, the suitable sequence in the use of the various types of resins depending upon the impure product to be purified and the slightly acidic environment during adsorption all enable one to obtain a high degree of purity in the final product. The process of the invention also results in elimination of the use of chlorinated organic solvents and generally leads to excellent yields during the purification.

DETAILED DESCRIPTION OF THE INVENTION

Process of the invention is described in greater detail in the following examples.

EXAMPLE 1

Purification of 4-demethoxy-daunorubicin

Impure 4-demethoxy-daunorubicin (15 g), having a titer of 70.2% and an impurity content of 18% was dissolved in 3.6 l of an 0.5% solution of sodium acetate. The solution, after being brought to pH 4.7 by the addition of acetic acid, was adsorbed in 400 ml of Amberlite XAD2 ® (Rohm and Haas) resin in a column having a diameter of 2.5 cm. The product was washed with 1000 ml of water and then eluted with a mixture of water-methanol (5:1 v/v). As a first eluate, 2000 ml of solution containing aglycones and various impurities were collected.

Elution was continued with mixture of water-methanol (1:1 v/v) and a 4500 ml fraction was collected. This fraction contained 4-demethoxy-daunorubicin along with 10% of impurities.

This fraction was brought to pH 2.8 by the addition of hydrochloric acid and then vacuum concentrated to a volume of 1500 ml. By adding sodium acetate to the concentrated solution, the pH was brought to 4.0 and the slightly acidic solution was adsorbed on 150 ml of CM Sepharose Cl 6B ® (Pharmacia) resin in a column having a diameter of 2.5 cm and a flow rate of 150 ml/hr. Upon completion of the adsorption, the column was first washed with 450 ml of water and then eluted with 0.03% hydrochloric acid.

The first 800 ml of eluate, containing 18% of impurities, were brought to pH 4.7 by the addition of a sodium acetate and collected for recycling to a solution of impure 4-demethoxy-daunorubicin which is to be adsorbed on the Amberlite XAD2 resin for the first purification stage.

The succeeding eluate (3500 ml), containing pure 4-demethoxy-daunorubicin was vacuum concentrated to a volume of 50 ml. To the resulting concentrate, 250 ml of acetone were added. The obtained precipitate was filtered, washed with acetone and dried. With a yield of 52%, as calculated on the starting impure product, 4-demethoxy-daunorubicin was obtained at a titer of 97% and an impurity content of less than 3%.

EXAMPLE 2

Purification of daunorubicin 15.0 g of impure daunorubicin by hydrochloride, having a titer of 74.2% and an impurity content of 8.5% were dissolved in 4500 ml water. The solution was brought to pH 5.0 by the addition of sodium acetate and adsorbed on 400 ml of S112 ® (Kastell) resin or Amberlite ER180 ® (Rohm and Haas) resin in a column having a diameter of 2.5 cm at a flow rate of 600 ml/hr (1.5 b/v).

The product was washed with 1000 ml of a 1% solution of sodium chloride and then eluted with a mixture of water-ethanol (1:1 v/v).

The head fraction (400 ml) containing the aglycones in solution was removed and elution was continued collecting 260 ml of eluate containing pure daunorubicin. The pH was adjusted to 2.5 by the addition of dilute hydrochloric acid, after which acetone was added and the product was allowed to crystallize at a temperature of 5° C. for 6 hours. The product was filtered, washed with acetone and vacuum dried for 12 hours.

With a yield of 80%, as calculated on the basis of the starting impure product, danorubicin is obtained with the following characteristics determined by HPLC: titer 97%; impurity content 2.6%.

EXAMPLE 3

Purification of 4-demethoxy-doxorubicin 2000 ml of an aqueous solution containing 10.4 g of 4-demethoxy-doxorubicin with an impurity content of 14% were adsorbed on 50 ml ER180® (Rohm and Haas) resin contained within a column having a diameter of 2.5 cm at a flow rate of 250 ml/hr.

The eluate, as partially purified by selective adsorption of the impurities, has then adsorbed on 200 ml CM Sepharose Cl 6B (Pharmacia) resin. The product was eluted with a mixture of methanol 50, water 50 and 0.015 concentrated hydrochloric acid. The head fraction (about 800 ml) containing aglycones and other impurities was discarded. 2000 ml of elutate containing the pure substance were then collected and vacuum concentrated to 60 ml. 300 ml acetone were added over a period of 3 hours with stirring. The resulting precipitate was filtered, washed with acetone and dried. With a yield of 58.2% based on the theoretical, 6.5 g of pure 4-demethoxy-doxorubicin were obtained with an impurity content of 3%.

EXAMPLE 4

Purification of 4'-desoxy-doxorubicin 15.0 g of 4'-desoxy-doxorubicin, having a titer of 69.2% ahd a 12% content of organic impurities as well as 12% of mineral salts, were dissolved in 2000 ml of water and adsorbed on 300 ml of CM Sephadex C25 resin at a flow rate of 600 ml/hr. Upon completion of the adsorption, the solution was eluted with 0.03% hydrochloric acid and a 6500 ml fraction was obtained containing 4'-desoxy-doxorubicin.

This fraction was brought to pH 3.8 by the addition of a solution of sodium hydrate, was adsorbed on 200 ml of S112 Kastel resin at a flow rate of 400 ml/hr. The product was washed with 600 ml of water and then eluted with methanol acidified to pH 2.0 by hydrochloric acid.

600 ml of eluate were obtained and then vacuum concentrated to 60 ml. Under stirring, the resulting concentrated solution was slowly poured into 600 ml of acetone. The precipitate which formed was filtered, washed with acetone and dried.

With a yield of 61% on theoretical, 4'-desoxy-doxorubicin is obtained with a titre of 95.8% and impurity contents of 4.2%.

EXAMPLE 5

Purification of 4'-epi-doxorubicin 15.0 g of impure 4'-epi-doxorubicin, having a titer of 75.9% and an impurity content of 15%, were dissolved in 4000 ml of water.

The solution was brought to pH 4.8 by the addition of sodium formate and adsorbed on 400 ml of Amberlite IRC 724 resin contained within a column having a diameter of 2.5 cm at a flow rate of 1600 ml/hr (4b.v.).

The column was washed with 800 ml of water and then eluted with a mixture of methanol 95, water 5 and concentrated hydrochloric acid 0.015. 4000 ml of eluate were collected containing 4'-epi-doxorubicin still containing 10% of impurities and a further 1500 ml of eluate containing primarily impurities were also collected.

The eluate containing 4'-epi-doxorubicin was concentrated to 1500 ml, brought to pH 4.8 by the addition of sodium formate and then adsorbed on 250 ml of Carboxymethylcellulose ® Wathman resin contained within a column having a diameter of 2.5 cm at a flow rate of 500 ml/hr (2b.v.).

Upon completion of the adsorption, the product was washed with a mixture of ethanol 99.3, water 0.7 and concentrated hydrochloric acid 0.015, and then eluted with a mixture of ethanol 90, water 10 and concentrated hydrochloric acid 0.05 to collect 3200 ml of eluate.

The eluate was vacuum concentrated to 60 ml and the product was precipitated by the addition of 300 ml of acetone.

6.9 g of 4'-epi-doxorubicin were obtained, having a titer of 91.2% and an impurity content of 3%. Yield =55.3%.

EXAMPLE 6

Purification of doxorubicin (a) 70 g of doxorubicin were dissolved in 20 l of water. The pH was brought to 3.7-4.5 by the addition of a buffer and the solution was adsorbed on 2 l of S112 Kastell ® resin contained within a column having a diameter of 6 cm. The product was eluted with a mixture of 35 l of water and 15 l of methanol.

The eluate (40 l) was vacuum concentrated to 0.5 l and the product was crystallized by the addition of a mixture of 1 l of ethanol and 4.5 l of acetone with stirring at 5° C. for 3 hours.

The product was filtered, washed with 0.8 l of acetone and vacuum dried at 40° C. for 5 hours.

56.0 g of partially purified doxorubicin (I) were obtained.

(b) 80.0 g partially purified doxorubicin (I), as obtained by the process of Example 6(a), were dissolved in 24 l of water and brought to pH 4.0 by the addition of a buffer.

The solution was adsorbed on a column having a diameter of 12 cm and containing 1.6 l of carboxymethlcellulose Wathman resin.

The column effluent was removed.

After washing with 3.2 l of water, the product was eluted with 55 l of water and brought to pH 2.5 by the addition of hydrochloric acid.

46 l of eluate were collected and vacuum concentrated to a volume of 0.6 l and the product was allowed to crystallize by careful addition of a mixture of isopropanol:acetone 1:3.

The product was filtered, washed with 1 l of acetone and dried at 40° C. for 4 hours.

65 g of doxorubicin were obtained with a titer of 98.5% and an impurity content of 1.5%.

Variations and modifications can, of course, be made without departing from the spirit and scope of the invention.

Having thus described out invention what we desire to secure by Letters Patent and hereby claim is:

1. A process for the purification of raw 4-demethoxy-daunorubicin having a titer of about 70.2% and containing as much as 18% of impurities obtained by a fermentation or synthetic method, whereby organic and inorganic impurities are removed therefrom said process comprising adsorbing an aqueous solution of the raw 4-demethoxy-daunorubicin, having a pH of about 4.7 and a concentration of about 0.4%, on an ion exchange resin which is Amberlite XAD2 ®, the ratio of resin to 4-demethoxy-daunorubicin being about 26:1 v/w, de-adsorbing the 4-demethoxy-daunorubicin by elution with a 5:1 v/v mixture of water and methanol, re-adsorbing the eluate after vacuum concentration thereof, and at a pH of about 4 on CM Sepharose CI 6B, de-adsorbing the further purified 4-demethoxy-daunorubicin by elution with 0.03% hydrochloric acid, concentrating the elutate in vacuo and then isolating the so purified 4-demethoxy-daunorubicin, whereby the thusly isolated product contains not more than about 3% of impurities at a titer of about 97%.

2. A process for the purification of a raw daunorubicin having a titer of about 74.2% and containing as much as 8.5% of impurities obtained by a fermentation or synthetic method, whereby organic and inorganic impurities are removed therefrom, said process comprising adsorbing an aqueous solution of the raw daunorubicin, having a pH of about 5 and a concentration of about 0.3%, on an ion exchange resin which is S112 Kastell ® or Amberlite ER180 ®, the ratio of resin to daunorubicin being about 26:1 v/w, deadsorbing the daunorubicin by elution with a 1:1 v/v mixture of water and ethanol and isolating the purified daunorubicin, whereby the thusly isolated product contains less than 2% of impurities with a titer of about 97%.

3. A process for the purification of a raw 4-demethoxy-doxorubicin containing as much as 14% of impurities and obtained by a fermentation or synthetic method, whereby organic and inorganic impurities are removed therefrom, said process comprising passing an aqueous solution of the raw 4-demethoxy-doxorubicin having a concentration of about 0.5% through an ion exchange resin which is Amberlite ER180 ®, the ratio of resin to 4-demethoxy-doxorubicin being about 4.8:1 v/w whereby a portion of the impurities are adsorbed on the resin, re-adsorbing the eluate on CM Sepharose CI 6B and deadsorbing the further purified 4-demethoxy-doxorubicin by elution with a 1:1 v/v mixture of slightly acidic water and methanol, concentrating the eluate in vacuo and then isolating the so purified 4-demethoxy-doxorubicin, whereby the thusly isolated product contains only about 3% of impurities.

4. A process for the purification of a raw 4'-desoxy-doxorubicin having a titer of about 69.2% and containing as much as 12% of organic impurities and 12% of mineral salts obtained by a fermentation or synthetic method, whereby organic and inorganic impurities are removed therefrom, said process comprising adsorbing an aqueous solution of the raw 4'-desoxy-doxorubicin, having a concentration of about 0.75%, on an ion exchange resin which is CM Sephadex C25 ®, the ratio of resin to 4'-desoxy-doxorubicin being about 20:1 v/w, de-adsorbing the 4'-desoxy-doxorubicin by elution with slightly acidic water, re-adsorbing the eluate at a pH of about 3.8 on S112 Kastell ® resin, de-adsorbing the further purified 4'-desoxy-doxorubicin by elution with methanol at about pH 2, concentrating the eluate in vacuo and then isolating the so purified 4'-desoxy-doxorubicin, whereby the thusly isolated product contains not more than about 4% of impurities at a titer of about 96%.

5. A process for the purification of a raw 4'-epi-doxorubicin having a titer of about 75.9% and containing as much as 15% of impurities obtained by a fermentation or synthetic method, whereby organic and inorganic impurities are removed therefrom said process comprising adsorbing an aqueous solution of the raw 4'-epi-doxorubicin, having a pH of about 4.8 and a concentration of about 0.4%, on an ion exchange resin which is Amberlite IRC 724 ®, the ratio of resin to 4'-epi-doxorubicin being about 26:1 v/w, de-adsorbing the 4'-epi-doxorubicin by elution with a 19:1 v/v mixture of slightly acidic methanol and water, readsorbing the eluate, which contains about 10% of impurities after vacuum concentration thereof and at a pH of about 4.8 on carboxymethyl cellulose, de-adsorbing the further purified 4'-epi-doxorubicin by elution with a 9:1 v/v mixture of slightly acidic ethanol and water, concentrating the eluate in vacuo and then isolating the so purified 4'-epi-doxorubicin, whereby the thusly isolated product contains not more than about 3% of impurities at a titer of about 91%.

6. A process for the purification of a raw doxorubicin obtained by a fermentation or synthetic method, whereby organic and inorganic impurities are removed therefrom, said process comprising adsorbing an aqueous solution of the raw doxorubicin, having a pH of about 4 and a concentration of about 0.3%, on an ion exchange resin which is carboxymethyl cellulose, the ratio of resin to doxorubicin being about 20:1 v/w, de-adsorbing the doxorubicin by elution with a slightly acidic water, concentrating the eluate in vacuo and then isolating the so purified doxorubicin, whereby the thusly isolated product contains not more than about 1.5% of impurities at a titer of about 98%.

* * * * *

UNITED STATES PATENT AND TRADEMARK OFFICE
CERTIFICATE OF CORRECTION

PATENT NO. : 4,861,870

DATED : August 29, 1989

INVENTOR(S) : Ernesto Oppici, Carlo Varesio and Onorino Giacoma Rosa

It is certified that error appears in the above-identified patent and that said Letters Patent is hereby corrected as shown below:

Title page, left hand column:

Under "United States Patent" change "Oppico et al" to --Oppici et al.--

Change the spelling of the surname of the first listed inventor as follows:

Change "Oppico" to --Oppici--

Signed and Sealed this

Twenty-second Day of October, 1991

Attest:

HARRY F. MANBECK, JR.

*Attesting Officer*     *Commissioner of Patents and Trademarks*